United States Patent [19]

Mills et al.

[11] Patent Number: 5,080,663
[45] Date of Patent: Jan. 14, 1992

[54] SEWING DEVICE

[75] Inventors: Timothy N. Mills; Christopher P. Swain; Geoffrey Brown, all of London, England

[73] Assignee: Univerity College London, London, England

[21] Appl. No.: 589,000

[22] Filed: Sep. 26, 1990

[51] Int. Cl.⁵ .............................................. A61B 17/00
[52] U.S. Cl. .................................. 606/144; 606/139; 606/188
[58] Field of Search ............... 606/144, 145, 148, 117, 606/139; 112/169, 199

[56] References Cited

U.S. PATENT DOCUMENTS

| | | | |
|---|---|---|---|
| 3,943,935 | 3/1976 | Cameron | 606/188 |
| 4,235,238 | 11/1980 | Ogiu et al. | 606/145 |
| 4,586,502 | 5/1986 | Bedi et al. | 606/144 |
| 4,841,888 | 6/1989 | Mills et al. | 606/145 |
| 4,931,060 | 6/1990 | Aué606 | 188/ |
| 4,943,294 | 7/1990 | Knapp | 606/188 |

Primary Examiner—Stephen C. Pellegrino
Assistant Examiner—Gary Jackson
Attorney, Agent, or Firm—Darby & Darby

[57] ABSTRACT

A sewing device is described for use in surgical procedures inside a patient, which can be used without the need to make an external incision in the patient. The device comprises a slot to which suction is applied at a plurality of locations to suck in a double-layer of tissue, and a needle for passing a tag into and through the double layer. The tag may have an article attached thereto, for example a sensor/transmitter.

15 Claims, 4 Drawing Sheets

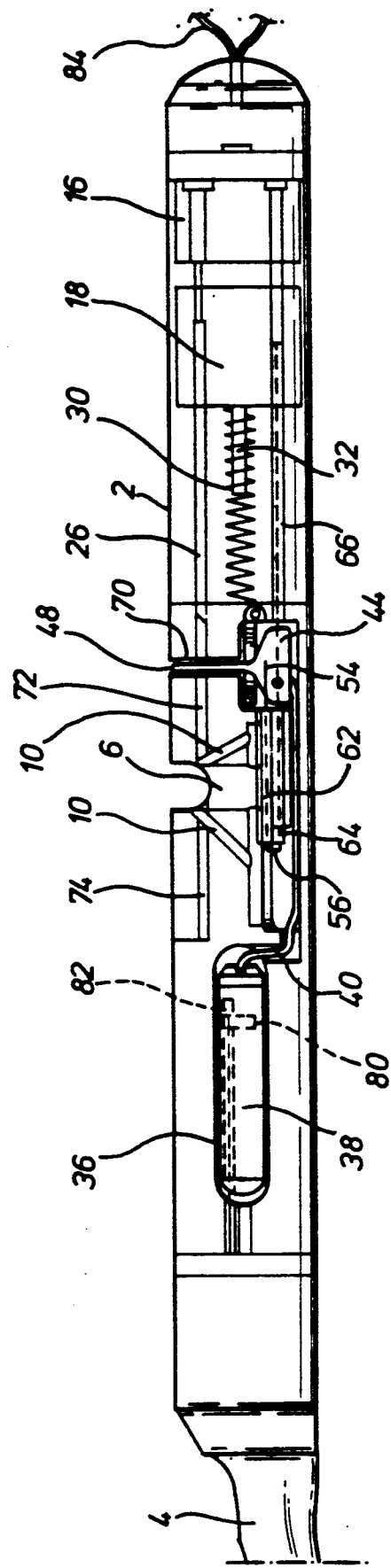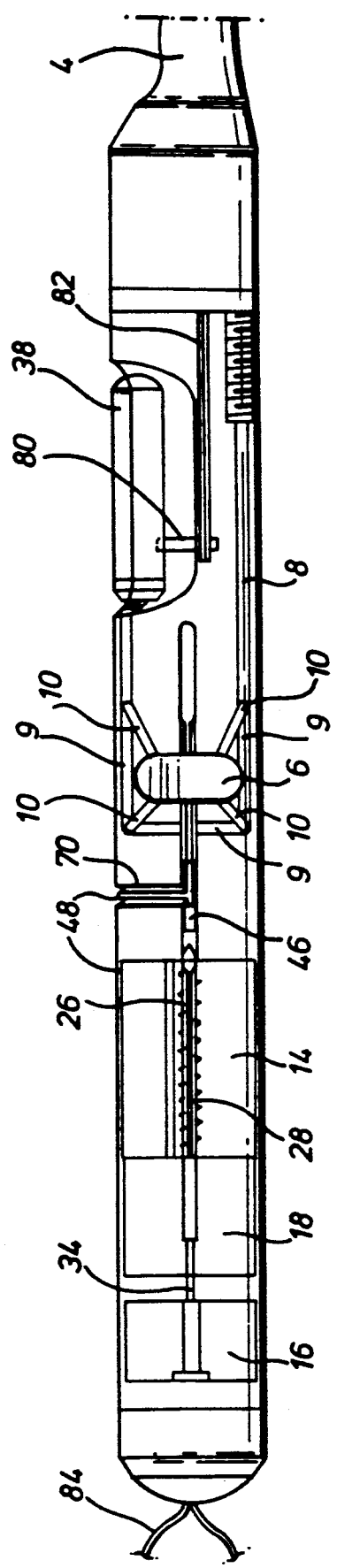

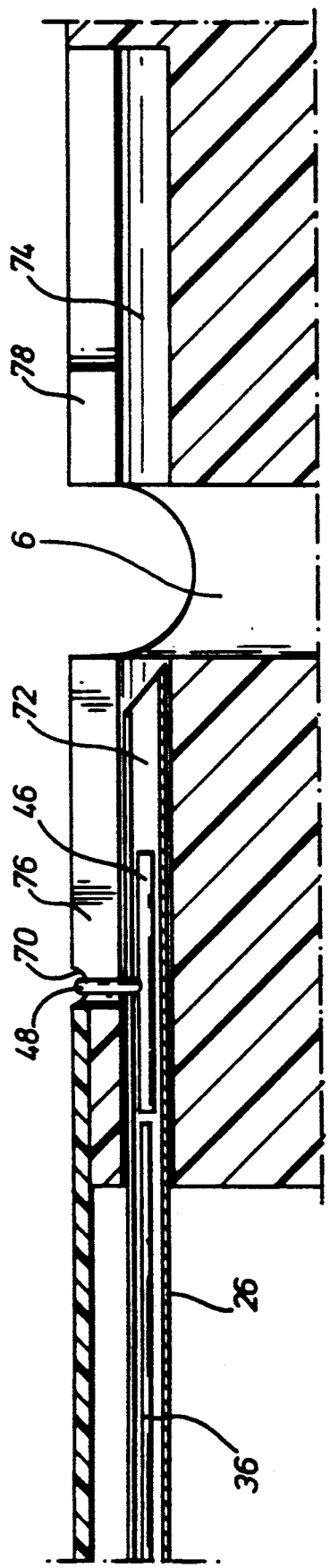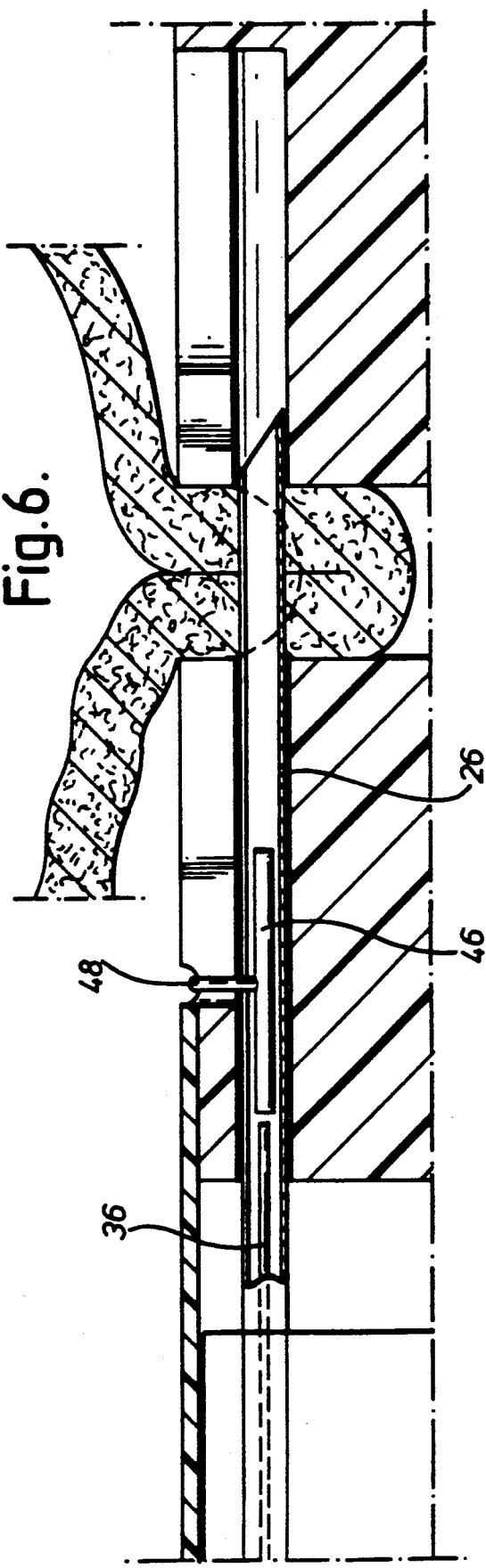

SEWING DEVICE

FIELD OF THE INVENTION

This invention relates to a sewing device for use in surgical procedures and, more particularly, relates to a device which can be used inside the body of a patient without the need to make an external incision in the patient, the machine being controlled externally of the patient, for example by endoscopic means. Devices of this general type are described in GB-A-2165559.

BACKGROUND AND SUMMARY OF THE INVENTION

An object of the invention is to provide a device for sewing an article to tissue, for example to the lining of the stomach. One example of such an article is a sensor provided with a radio transmitter, for detecting and transmitting to an external receiver information about some parameter relating to the interior of the patient. Another example is an article provided with a slow-release drug for administration to the patient.

Another object of the invention is to provide a sewing device for use in surgical procedures, in which each stitch is formed by a separate stitch member.

Yet another object is to provide a sewing device having improved suction means for holding a double layer of tissue in a slot to enable a stitch to be formed in the tissue.

According to one aspect of the invention there is provided a sewing device for attaching an article to the interior tissue of a patient, which comprises a body provided with means for releasably holding the said article, and a stitching means provided on the body for attaching the said article to the interior tissue of the patient.

According to another aspect of the invention there is provided a sewing device for use on the interior tissue of a patient, which comprises a body provided with means for releasably holding a stitch member, a sewing means for inserting the stitch member into and through a piece of the said tissue to form a single discrete stitch.

Preferably the single stitch is in the form of a tag, such tag conveniently having the general shape of an "I".

According to yet another aspect of the invention there is provided a sewing device comprising suction means for holding a double layer of tissue in a slot, said suction means applying suction to the tissue at a plurality of locations, and means for inserting a stitch into and through said double layer.

The invention is further described below with reference to the accompanying drawings, in which:

FIG. 1 is a plan view of an embodiment of the invention;

FIG. 2 is a side elevation of the embodiment;

FIGS. 5, 6 and 7 are views of a portion of the device, on a still larger scale, showing successive steps in its operation.

It should be made clear that although the terms "plan view" and "elevation" are used in the above description of the drawings, these terms are used arbitrarily, and the device is not to be regarded as having any particular orientation which can be said to be its right way up.

The device illustrated comprises a body 2 of a size which enables the device to be introduced into the stomach of an adult patient via the mouth. Thus, for example, the body may be 145 mm in length and 14 mm in diameter. These dimensions are, of course, given only by way of example. The body is shown as being transparent, so that the internal components thereof are visible, and indeed it may be transparent, being formed of a suitable transparent plastics material. However, it is not an essential requirement that the body should be transparent. The body is attached to an operating device (not shown) via an array of tubes, some of which carry cables, held in a tubular sheath 4. The tubes and cables may be of the order of 1 m in length, so that the operating device is external of the patient and a suitable distance away from the patient.

Figure 4:
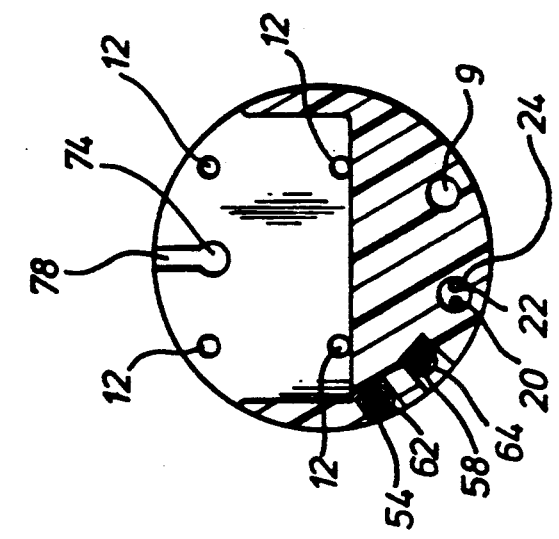
FIG. 4 is a cross-section taken on line X—X in FIG. 3.

The body is provided intermediate its ends with a cavity 6. The cavity is open to the exterior of the body on one side. One of the tubes within the sheath 4 is connected at its distal end to a source of vacuum, and at its proximal end is connected to a vacuum duct 8 formed within the body 2. The duct 8 communicates with the cavity 6 via an array of ductlets 9 and 10, so arranged that each of the ductlets 10 is open to the cavity 6 at a port 12, there being four ports 12 on each side of the cavity. One side of the cavity can be seen in FIG. 4, with its four ports 12. Suction is thus applied to the slot at a plurality of locations.

At its end remote from the sheath 4, the body 2 is hollow and defines a cylindrical chamber 14. Two pistons 16 and 18 are mounted so as to be slidable longitudinally within the chamber 14. The pistons 16 and 18 are connected to the operating device by wires 20 and 22 which can be seen in FIG. 4 in a tube 24. The wire 22 is connected to one end of a hollow tube (not shown) the other end of which is connected to the piston 18. The wire 20 passes slidably through the hollow tube and is connected to the piston 16. Thus, the pistons 16 and 18 are movable independently of one another by the wires 20 and 22 respectively.

The piston 18 has one end of a hollow needle 26 secured thereto. The needle 26 has a longitudinal slot 28 which opens into the interior thereof and extends to the tip of the needle. A compression spring 30 serves to bias the piston 18 towards the distal end of the body, the spring being held in place by having one end thereof surrounding a cylindrical boss 32 which protrudes from the piston 18. The piston 16 carries a cylindrical pushing member 34 which extends into, and is slidable along, the hollow bore of the needle 26.

The body 2 is provided with an elongate, longitudinally extending load cavity 36. The cavity is open towards the exterior of the body and an article which it is desired to attach to the interior of the patient is placed in the cavity. The drawings show a load 38 which may, for example, be a sensor provided with a radio transmitter, for detecting and transmitting to an external receiver information about some parameter relating to the interior of the patient.

It should be noted, however, that the load cavity may be omitted, in which case the sewing device can be used for a pure sewing operation without attaching any article to the tissue.

The article 38 is attached by a flexible cord 40 to a tag 42. This is shown most clearly in FIG. 3, where, however, the central portion of the cord is broken away so as not to obscure the underlying components of the device. The tag 42 is generally I-shaped. It has a flat head 44 at one end, a cross-piece 46 at the other end and a connecting member 48 extending between the head 44 and the cross-piece 46. The tag may be made from a suitably inert plastics material, and the connecting member 48 is of sufficiently small diameter to be very flexible. The tag may alternatively be made of some other material, for example an absorbable suture material such as catgut. The tag 42 is used to form the stitch by means of which the device sews the article 38 to the patient, as will be explained below.

The head 44 is received in a recess 50 formed in the external surface of the body 2. On its base, the recess 50 has a leaf spring 52 which, when the recess is empty, protrudes a certain distance above the base. When the head 44 is pushed into the recess 50 it urges the leaf spring 52 towards the base, and the head is held in the recess by an arm 54 of a U-shaped slider 56. The U-shaped member 56 has a second arm 58, and the arms 54 and 58 are respectively slidable in fixed tubes 62 and 64. The piston 18 carries a rod 66 the lefthand portion of which (as viewed in FIGS. 1 and 3) is hollow, and the righthand portion of which is not, or is blocked off. The end of the arm 58 is received in the hollow portion of rod 66. When the piston 18 moves leftwardly (as viewed in FIGS. 1 and 3) the rod 66 moves likewise, and the portion of the rod 66 which is not hollow engages the end of the arm 58 and moves the whole U-shaped member 56 leftwardly. Movement of the piston 18 in the opposite direction leaves the position of the U-shaped member 56 unaffected.

The connecting member 48 of the tag 42 runs in an annular groove 70 formed in the external surface of the body 2. The cross-piece 46 of the tag is received in a longitudinal bore 72 formed within the body, as can be seen most clearly in FIG. 5. The bore 72 opens at one end into the cavity 6, and is aligned with a further bore 74 which opens into the cavity on the opposite side. The bores 72 and 74 communicate laterally with the exterior of the body 2 by slots 76 and 78 respectively. These slots are narrower than the diameter of the bores, and the cross piece 46 is of larger diameter than the width of the slots. Thus, once the cross-piece 46 is inserted in the bore 72 it cannot be pulled out of the bore through the slot 76.

The operation of the device is as follows. Firstly, the cross-piece 46 is inserted into the bore 72 via the cavity 6, and positioned so that the connecting member 48 can be received in the annular recess 70. The cross-piece 46 enters the interior of the needle 26 through the slot 28. The head 44 is then placed in the recess 50 and the U-shaped member 56 is slid manually to the right (as viewed in FIG. 3) so that the arm 54 retains it in the recess against the force of the leaf spring 52. The article 38, already attached to the tag 42 by the cord 40, is then placed in the load cavity 36. At this point it should be noted that a leaf spring 80 is provided at the bottom of the load cavity 36, the spring 80 running across the cavity in a recess provided in the base thereof. Before the article 38 is introduced into the load cavity 36 the leaf spring 80 is held down in its recess by moving a rod 82 longitudinally to the right, as viewed in FIG. 1 (or longitudinally to the left, as viewed in FIG. 2). The rod 82 is connected at its proximal end to a cable (not shown) which runs in one of the tubes in the sheath 4.

With the device now ready for use, it is introduced into the patient, for example introduced into the stomach of a patient via the mouth. To assist in positioning the device correctly, a loop of thread 84, shown in part in each of FIGS. 1 and 2, is provided at the forward end of the body. The device may be manipulated via the loop 84 using a pair of forceps introduced into the patient through a catheter.

The body 2 is positioned so that the open face of the cavity 6 is adjacent the tissue to which the article 38 is to be attached. The source of suction is then operated, which causes a U-shaped piece of tissue to be sucked into the cavity 6, as shown in FIG. 6. By applying suction at a plurality of locations the tissue can be held more reliably than by using only a single location as in GB-A-2165559.

Then, as also shown in FIG. 6, the hollow needle 26 is moved along the bore 72, across the cavity 6, and into the bore 74, thus passing through both layers of the piece of tissue. The needle is moved by moving the piston 18 to which it is attached. The tag 42 is not moved as a result of movement of the needle, because the diameter of the cross-piece 46 is less than the internal diameter of the needle, and the diameter of the connecting member 48 is less than the width of the slot 28 in the needle.

Figure 3:
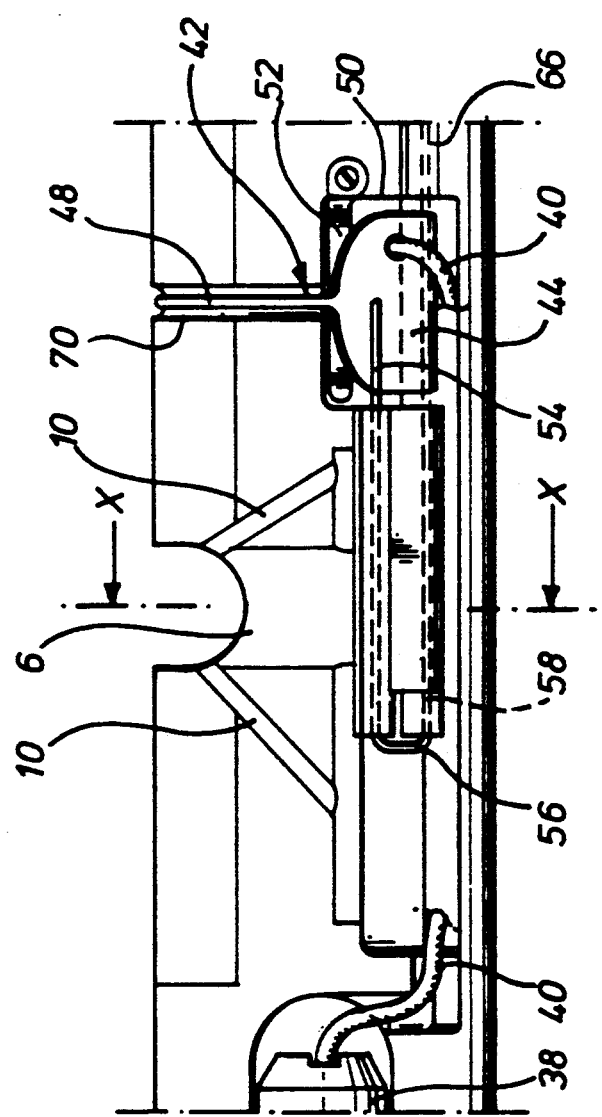
FIG. 3 is a view similar to FIG. 1 but showing only a portion of the device, on a larger scale.

Moving the piston 18 also has the effect of moving the rod 66, thus causing the U-shaped member 56 to move leftwardly as shown in FIG. 3, and so releasing the head 44 of the tag 42 from the recess 50.

At this point, or at some point in the preceding operations, the article 38 is released from the load cavity 36. This is done by moving the rod 82 to disengage it from the leaf spring 80, which is then able to spring away from the base of the load cavity, expelling the article 38.

Figure 7:
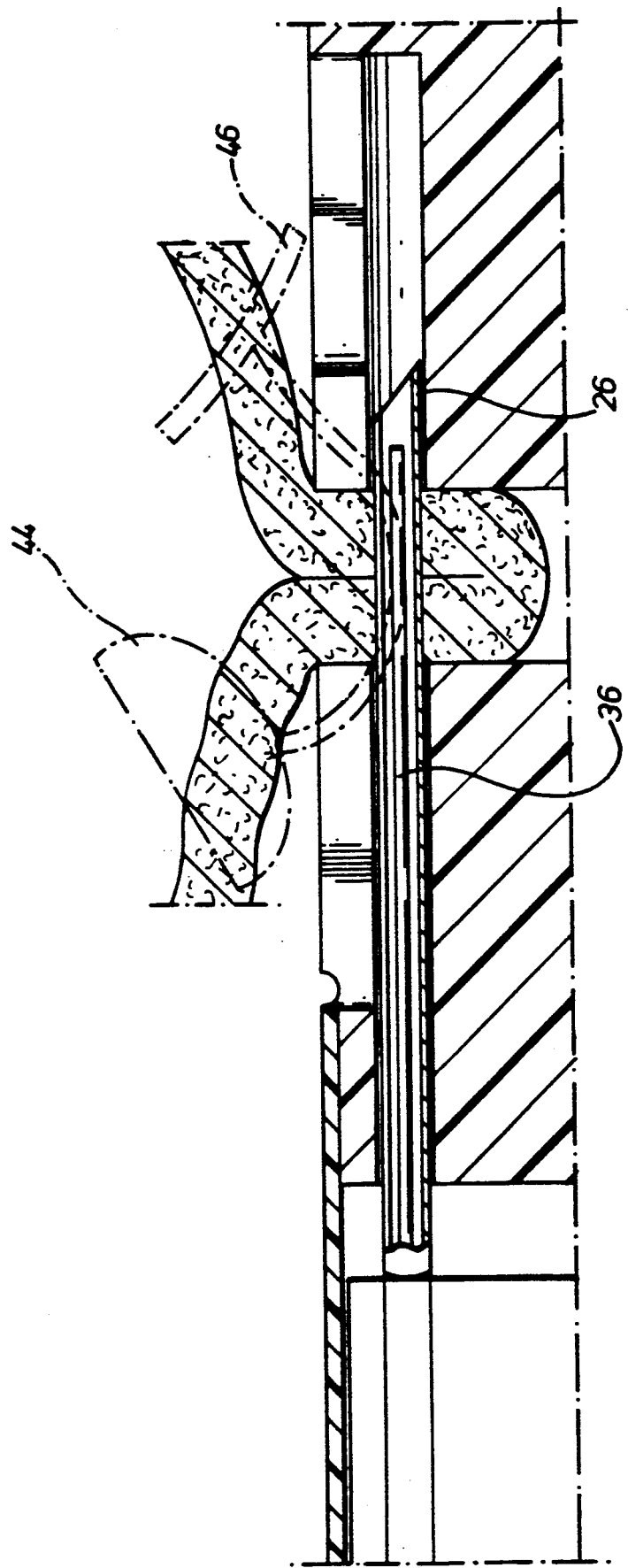

The piston 16 is then moved leftwardly as shown in FIG. 1 (or rightwardly as shown in FIG. 2) which causes the pusher rod 36 to move along the hollow needle, engaging the cross-piece 46 and pushing the cross-piece out of the end of the needle. This is as shown in FIG. 7. The needle is then withdrawn to its original position, leaving the tag extending through the U-shaped piece of tissue, with the article 38 thereby attached to the tissue via the cord 40. The compression spring 30 helps to reduce the risk of the needle being jammed in the tissue.

It is to be understood that the idea of a load cavity can be applied not only to devices in which the sewing is effected by inserting a single stitch in the form of a tag, but also to devices, for example, as shown in GB-A-2165559, where a continuous thread is used.

It is further to be noted that the use of a suction cavity in which suction is applied at a plurality of locations (by way of example, eight such locations as in the embodiment described), as opposed to a single location as described in GB-A-2165559, is believed to be novel and inventive in its own right. Accordingly, the present invention is intended to cover all sewing devices (whether using single stitches in the form of tags, or not) and all stapling devices, which employ the use of suction at a plurality of locations whether or not such devices are provided with means for releasably holding an article for attachment to a patient.

We claim:

1. A sewing device for attaching an article to the interior tissue of a patient, which comprises a body provided with means for releasably holding the article, and a stitching means provided on the body for attaching the article to the interior tissue of the patient, wherein the releasable holding means comprises a cavity formed in the body and open to the exterior thereof, and wherein the cavity is provided with an expelling means operable to urge the article out of the cavity.

2. A device according to claim 1, wherein the said expelling means comprises a spring member located in the cavity, and a spring holding member movable between a first position in which it prevents the spring member urging the article out of the cavity and a second position in which it permits the spring member to urge the article out of the cavity.

3. A device according to claim 1, comprising means, provided on the body, for holding a U-shaped double layer of tissue, the stitching means being adapted to attach the said article to the tissue.

4. A device according to claim 3, wherein the means for holding the said double layer comprises a slot formed in the body and open to the exterior thereof and means for applying suction to the slot.

5. A sewing device for use in surgical procedures, comprising a body having an external surface, means provided on the body for holding a U-shaped double layer of tissue, and stitching means for inserting into and through the tissue a stitch member to form a single discrete stitch, said stitch member being in the form of a tag and having a head portion, a crosspiece and a connecting portion connecting said head portion and said crosspiece, and wherein the device has a body adapted to hold said tag, with said tag having a rest position in which it does not extend beyond the external surface of the body, the device being provided with a head-retaining member which is movable from a rest position to a head-releasing position in which the head of said tag extends beyond said external surface, and wherein the stitching means comprises an elongate needle movable from a first position corresponding to a rest position to a second position in which at least the tip of the needle passes through the tissue, said needle having a longitudinal bore therein which communicates with the exterior of said needle via a longitudinal slot at least over a portion of the needle adjacent the tip, whereby said cross-piece of said tag can be received in the longitudinal bore, said stitching means further comprising a pushing member movable longitudinally within the longitudinal bore to expel the cross-piece therefrom after the tip of said needle has passed through the tissue.

6. A device according to claim 5, wherein the said body is recessed on the external surface thereof to receive the head and connecting portion of the tag.

7. A device according to claim 6, wherein the head of the tag is retained on the recessed external surface by said head retaining member, which is movable from a head retaining position to said head releasing position.

8. A device according to claim 7, wherein the body is hollow and has a pair of pistons therein which are movable longitudinally independently of one another, one piston carrying the needle and head-retaining member, and the other piston carrying the pushing member.

9. A device according to claim 5 which comprises a body, and wherein the means for holding a U-shaped double layer of tissue comprises a slot formed in the body and open to the exterior thereof and means for applying suction to the slot.

10. A device according to claim 9, wherein the suction applying means is effective to apply suction to the slot at a plurality of locations.

11. A device according to claim 5, which comprises a body, and wherein the body is provided with means for releasably holding an article to be attached to said tissue by the said stitch member.

12. A device according to claim 11, wherein the releasable holding means comprises a cavity formed in the body and open to the exterior thereof.

13. A device according to claim 12, wherein said expelling means comprises a spring member located in a cavity, and has a spring holding member movable between a first position in which it prevents the spring member urging the said article out of the cavity and a second position in which it permits the spring member to urge the said article out of the cavity.

14. A device according to claim 10, wherein the cavity is provided with an expelling means operable to urge the article out of the cavity.

15. A sewing device for use in surgical procedures, comprising means for holding a U-shaped double layer of tissue, and stitching means for inserting into and through the double layer a stitch member to form a single discrete stitch, said device including a body and wherein the body is provided with means for releasably holding an article to be attached to the double layer of tissue by said stitch member, said releasable holding means comprising a cavity formed in said body and open to the exterior thereof, said cavity having a spring member therein, and wherein said device has a spring holding member movable between a first position in which it prevents the spring member urging the article out of the cavity and a second position in which it permits the spring member to urge the article out of the cavity.

* * * * *